(12) United States Patent
Fulkerson et al.

(10) Patent No.: US 9,352,282 B2
(45) Date of Patent: *May 31, 2016

(54) MANIFOLDS FOR USE IN CONDUCTING DIALYSIS

(75) Inventors: Barry N. Fulkerson, Longmont, CO (US); Russell T. Joseph, Las Flores, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 874 days.

This patent is subject to a terminal disclaimer.

(21) Appl. No.: 13/337,227

(22) Filed: Dec. 26, 2011

(65) Prior Publication Data

US 2012/0090706 A1  Apr. 19, 2012

Related U.S. Application Data

(63) Continuation of application No. 12/237,914, filed on Sep. 25, 2008, now Pat. No. 8,105,487.

(60) Provisional application No. 60/975,157, filed on Sep. 25, 2007.

(51) Int. Cl.
| *B01D 61/30* | (2006.01) |
| *A61M 1/00* | (2006.01) |
| *B01D 61/18* | (2006.01) |
| *A61M 1/16* | (2006.01) |
| *A61M 1/36* | (2006.01) |

(52) U.S. Cl.
CPC ............ *B01D 61/30* (2013.01); *A61M 1/1696* (2013.01); *B01D 61/18* (2013.01); *A61M 1/1692* (2013.01); *A61M 1/3639* (2013.01); *A61M 2205/126* (2013.01); *A61M 2205/3553* (2013.01); *A61M 2205/3584* (2013.01); *B01D 2313/10* (2013.01); *B01D 2313/105* (2013.01); *B01D 2313/12* (2013.01); *B01D 2313/125* (2013.01); *B01D 2313/243* (2013.01); *Y10T 137/8158* (2015.04); *Y10T 137/87153* (2015.04); *Y10T 137/87249* (2015.04)

(58) Field of Classification Search
None
See application file for complete search history.

(56) References Cited

U.S. PATENT DOCUMENTS

| 2,328,381 A | 8/1943 | Jaffe |
| 3,242,456 A | 3/1966 | Duncan |
| 3,388,803 A | 6/1968 | Scott |
| 3,420,492 A | 1/1969 | Ray |
| 3,669,878 A | 6/1972 | Marantz |

(Continued)

FOREIGN PATENT DOCUMENTS

| CN | 1235849 A | 11/1999 |
| CN | 1471617 A | 1/2004 |

(Continued)

OTHER PUBLICATIONS

Renal Solutions, Portions of the Allient Sorbent Hemodialysis System, Operator Manual, 2008, Chapters 1 to 2.

(Continued)

*Primary Examiner* — Krishnan S Menon
(74) *Attorney, Agent, or Firm* — Novel IP

(57) ABSTRACT

The present application discloses novel systems for conducting the filtration of blood using manifolds. The manifolds integrate various sensors and have fluid pathways formed therein to direct fluids from various sources through the requisite blood filtration or ultrafiltration system steps.

13 Claims, 8 Drawing Sheets

(56) References Cited

U.S. PATENT DOCUMENTS

| | | |
|---|---|---|
| 3,669,880 A | 6/1972 | Marantz |
| 3,709,222 A | 1/1973 | De Vries |
| 3,746,175 A | 7/1973 | Markley |
| 3,803,913 A | 4/1974 | Tracer |
| 3,814,376 A | 6/1974 | Reinicke |
| 3,850,835 A | 11/1974 | Marantz |
| 3,884,808 A | 5/1975 | Scott |
| 3,894,431 A | 7/1975 | Muston |
| 3,902,490 A | 9/1975 | Jacobsen |
| 3,946,731 A | 3/1976 | Lichtenstein |
| 3,961,918 A | 6/1976 | Johnson |
| 3,989,622 A | 11/1976 | Marantz |
| 3,989,625 A | 11/1976 | Mason |
| 3,994,799 A | 11/1976 | Yao |
| 4,000,072 A | 12/1976 | Sato |
| 4,071,444 A | 1/1978 | Ash et al. |
| 4,083,777 A | 4/1978 | Hutchisson |
| 4,094,775 A | 6/1978 | Mueller |
| 4,113,614 A | 9/1978 | Rollo |
| 4,118,314 A | 10/1978 | Yoshida |
| 4,209,392 A | 6/1980 | Wallace |
| 4,212,738 A | 7/1980 | Henne |
| 4,247,393 A | 1/1981 | Wallace |
| 4,267,040 A | 5/1981 | Schael |
| 4,269,708 A | 5/1981 | Bonomini |
| 4,326,955 A | 4/1982 | Babb |
| 4,348,283 A | 9/1982 | Ash |
| 4,354,562 A | 10/1982 | Newman |
| 4,368,737 A | 1/1983 | Ash |
| 4,371,385 A | 2/1983 | Johnson |
| 4,381,999 A | 5/1983 | Boucher |
| 4,387,777 A | 6/1983 | Ash |
| 4,397,189 A | 8/1983 | Johnson |
| 4,397,519 A | 8/1983 | Cooney |
| 4,402,694 A | 9/1983 | Ash et al. |
| 4,403,765 A | 9/1983 | Fisher |
| 4,403,984 A | 9/1983 | Ash et al. |
| 4,413,988 A | 11/1983 | Handt et al. |
| 4,430,098 A | 2/1984 | Bowman |
| 4,443,333 A | 4/1984 | Mahurkar |
| 4,460,555 A | 7/1984 | Thompson |
| 4,464,172 A | 8/1984 | Lichtenstein |
| 4,466,804 A | 8/1984 | Hino |
| 4,469,593 A | 9/1984 | Ishihara et al. |
| 4,477,342 A | 10/1984 | Allan |
| 4,480,483 A | 11/1984 | McShane |
| 4,498,902 A | 2/1985 | Ash et al. |
| 4,531,799 A | 7/1985 | Gray |
| 4,535,637 A | 8/1985 | Feller |
| 4,559,039 A | 12/1985 | Ash et al. |
| 4,563,170 A | 1/1986 | Aigner |
| 4,581,141 A | 4/1986 | Ash |
| 4,596,550 A | 6/1986 | Troutner |
| 4,599,055 A | 7/1986 | Dykstra |
| 4,606,826 A | 8/1986 | Sano |
| 4,630,799 A | 12/1986 | Nolan |
| 4,650,587 A | 3/1987 | Polak |
| 4,661,246 A | 4/1987 | Ash |
| 4,666,598 A | 5/1987 | Heath |
| 4,680,122 A | 7/1987 | Barone |
| 4,683,053 A | 7/1987 | Polaschegg |
| 4,710,164 A | 12/1987 | Levin |
| 4,740,755 A | 4/1988 | Ogawa |
| 4,750,705 A | 6/1988 | Zippe |
| 4,762,618 A | 8/1988 | Gummesson |
| 4,765,907 A | 8/1988 | Scott |
| 4,777,953 A | 10/1988 | Ash et al. |
| 4,806,247 A | 2/1989 | Schoendorfer |
| 4,826,663 A | 5/1989 | Alberti |
| 4,828,543 A | 5/1989 | Weiss |
| 4,828,693 A | 5/1989 | Lindsay |
| 4,831,884 A | 5/1989 | Drenthen |
| 4,854,322 A | 8/1989 | Ash et al. |
| 4,861,242 A | 8/1989 | Finsterwald |
| 4,885,942 A | 12/1989 | Magori |
| 4,897,189 A | 1/1990 | Greenwood |
| 4,909,713 A | 3/1990 | Finsterwald |
| 4,914,819 A | 4/1990 | Ash |
| 4,943,279 A | 7/1990 | Samiotes |
| 4,950,244 A | 8/1990 | Fellingham |
| 4,950,395 A | 8/1990 | Richalley |
| 4,968,422 A | 11/1990 | Runge |
| 4,990,258 A | 2/1991 | Bjare |
| 4,995,268 A | 2/1991 | Ash et al. |
| 4,997,570 A | 3/1991 | Polaschegg |
| 5,002,054 A | 3/1991 | Ash et al. |
| 5,011,607 A | 4/1991 | Shinzato |
| 5,032,261 A | 7/1991 | Pyper |
| 5,074,368 A | 12/1991 | Bullivant |
| 5,100,554 A | 3/1992 | Polaschegg |
| 5,114,580 A | 5/1992 | Ahmad et al. |
| 5,147,613 A | 9/1992 | Heilmann et al. |
| 5,152,174 A | 10/1992 | LaBudde |
| 5,157,332 A | 10/1992 | Reese |
| 5,161,779 A | 11/1992 | Graner |
| 5,170,789 A | 12/1992 | Narayan |
| 5,188,604 A | 2/1993 | Orth |
| 5,198,335 A | 3/1993 | Sekikawa et al. |
| 5,211,643 A | 5/1993 | Reinhardt et al. |
| 5,215,450 A | 6/1993 | Tamari |
| 5,228,308 A | 7/1993 | Day |
| 5,230,341 A | 7/1993 | Polaschegg |
| 5,230,614 A | 7/1993 | Zanger |
| 5,258,127 A | 11/1993 | Gsell |
| 5,259,961 A | 11/1993 | Eigendorf |
| 5,277,820 A | 1/1994 | Ash |
| 5,284,470 A | 2/1994 | Beltz |
| 5,284,559 A | 2/1994 | Lim |
| 5,295,505 A | 3/1994 | Polaschegg et al. |
| 5,304,349 A | 4/1994 | Polaschegg |
| 5,308,315 A | 5/1994 | Khuri et al. |
| 5,322,258 A | 6/1994 | Bosch |
| 5,322,519 A | 6/1994 | Ash |
| 5,346,472 A | 9/1994 | Keshaviah |
| 5,360,445 A | 11/1994 | Goldowsky |
| 5,385,005 A | 1/1995 | Ash |
| D355,816 S | 2/1995 | Ash |
| 5,391,143 A | 2/1995 | Kensey |
| 5,405,315 A | 4/1995 | Khuri et al. |
| 5,405,320 A | 4/1995 | Twardowski |
| 5,415,532 A | 5/1995 | Loughnane |
| 5,441,636 A | 8/1995 | Chevallet |
| 5,445,630 A | 8/1995 | Richmond |
| 5,460,493 A | 10/1995 | Deniega et al. |
| 5,468,388 A | 11/1995 | Goddard |
| 5,476,444 A | 12/1995 | Keeling et al. |
| D370,531 S | 6/1996 | Ash et al. |
| 5,536,412 A | 7/1996 | Ash |
| 5,540,265 A | 7/1996 | Polaschegg et al. |
| 5,545,131 A | 8/1996 | Davankov |
| 5,577,891 A | 11/1996 | Loughnane et al. |
| 5,580,460 A | 12/1996 | Polaschegg |
| 5,591,344 A | 1/1997 | Kenley |
| 5,609,770 A | 3/1997 | Zimmerman |
| 5,614,677 A | 3/1997 | Wamsiedler et al. |
| 5,616,305 A | 4/1997 | Mathieu |
| 5,624,551 A | 4/1997 | Baumann et al. |
| 5,629,871 A | 5/1997 | Love |
| 5,632,897 A | 5/1997 | Mathieu |
| 5,644,285 A | 7/1997 | Maurer |
| 5,674,390 A | 10/1997 | Matthews |
| 5,679,245 A | 10/1997 | Manica |
| 5,693,008 A | 12/1997 | Brugger |
| 5,698,083 A | 12/1997 | Glass |
| 5,711,883 A | 1/1998 | Folden et al. |
| 5,713,850 A | 2/1998 | Heilmann et al. |
| 5,725,773 A | 3/1998 | Polaschegg |
| 5,725,776 A | 3/1998 | Kenley |
| 5,744,027 A | 4/1998 | Connell |
| 5,762,782 A | 6/1998 | Kenley |
| 5,770,806 A | 6/1998 | Hiismaeki |
| 5,782,796 A | 7/1998 | Din et al. |
| 5,794,669 A | 8/1998 | Polaschegg et al. |
| 5,840,068 A | 11/1998 | Cartledge |

(56) References Cited

U.S. PATENT DOCUMENTS

| | | |
|---|---|---|
| 5,858,186 A | 1/1999 | Glass |
| 5,876,419 A | 3/1999 | Carpenter |
| 5,902,336 A | 5/1999 | Mishkin |
| 5,906,978 A | 5/1999 | Ash |
| 5,919,369 A | 7/1999 | Ash |
| 5,928,177 A | 7/1999 | Brugger |
| 5,938,938 A | 8/1999 | Bosetto |
| 5,944,684 A | 8/1999 | Roberts |
| 5,945,343 A | 8/1999 | Munkholm |
| 5,947,953 A | 9/1999 | Ash et al. |
| 5,951,870 A | 9/1999 | Utterberg |
| 5,980,481 A | 11/1999 | Gorsuch |
| 5,984,891 A | 11/1999 | Keilman |
| 5,989,423 A | 11/1999 | Kamen |
| 5,989,438 A | 11/1999 | Fumiyama |
| 6,042,561 A | 3/2000 | Ash et al. |
| 6,044,691 A | 4/2000 | Kenley |
| 6,086,753 A | 7/2000 | Ericson |
| 6,117,100 A | 9/2000 | Powers |
| 6,117,122 A | 9/2000 | Din |
| 6,156,007 A | 12/2000 | Ash |
| 6,168,578 B1 | 1/2001 | Diamond |
| 6,190,349 B1 | 2/2001 | Ash et al. |
| 6,196,922 B1 | 3/2001 | Hantschk |
| 6,196,992 B1 | 3/2001 | Keilman |
| 6,200,485 B1 | 3/2001 | Kitaevich |
| 6,217,540 B1 | 4/2001 | Yazawa et al. |
| 6,234,989 B1 | 5/2001 | Brierton et al. |
| 6,254,567 B1 | 7/2001 | Treu et al. |
| 6,264,611 B1 | 7/2001 | Ishikawa |
| 6,264,680 B1 | 7/2001 | Ash |
| 6,280,406 B1 | 8/2001 | Dolecek |
| 6,284,131 B1 | 9/2001 | Hogard |
| 6,287,516 B1 | 9/2001 | Matson et al. |
| 6,303,036 B1 | 10/2001 | Collins et al. |
| 6,325,774 B1 | 12/2001 | Bene |
| 6,332,985 B1 | 12/2001 | Sherman et al. |
| 6,348,162 B1 | 2/2002 | Ash |
| 6,406,631 B1 | 6/2002 | Collins |
| 6,409,699 B1 | 6/2002 | Ash |
| 6,416,293 B1 | 7/2002 | Bouchard |
| 6,468,427 B1 | 10/2002 | Frey |
| 6,471,872 B2 | 10/2002 | Kitaevich et al. |
| 6,487,904 B1 | 12/2002 | Myhre |
| 6,491,656 B1 | 12/2002 | Morris |
| 6,491,673 B1 | 12/2002 | Palumbo |
| 6,497,675 B1 | 12/2002 | Davankov |
| 6,517,045 B1 | 2/2003 | Northedge |
| 6,551,513 B2 | 4/2003 | Nikaido et al. |
| 6,554,789 B1 | 4/2003 | Brugger et al. |
| 6,561,997 B1 | 5/2003 | Weitzel |
| 6,565,395 B1 | 5/2003 | Schwarz |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,579,460 B1 | 6/2003 | Willis et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,607,495 B1 | 8/2003 | Skalak |
| 6,610,036 B2 | 8/2003 | Branch |
| 6,623,470 B2 | 9/2003 | Munis et al. |
| 6,627,164 B1 | 9/2003 | Wong |
| 6,632,192 B2 | 10/2003 | Gorsuch |
| 6,638,477 B1 | 10/2003 | Treu et al. |
| 6,638,478 B1 | 10/2003 | Treu et al. |
| 6,649,063 B2 | 11/2003 | Brugger et al. |
| 6,653,841 B1 | 11/2003 | Koerdt et al. |
| 6,673,314 B1 | 1/2004 | Burbank et al. |
| 6,681,624 B2 | 1/2004 | Furuki |
| 6,685,664 B2 | 2/2004 | Levin |
| 6,690,280 B2 | 2/2004 | Citrenbaum |
| 6,695,803 B1 | 2/2004 | Robinson |
| 6,702,561 B2 | 3/2004 | Stillig et al. |
| 6,706,007 B2 | 3/2004 | Gelfand |
| 6,730,266 B2 | 5/2004 | Matson et al. |
| 6,743,193 B2 | 6/2004 | Brugger et al. |
| 6,758,975 B2 | 7/2004 | Peabody |
| 6,764,460 B2 | 7/2004 | Dolecek et al. |
| 6,773,412 B2 | 8/2004 | OMahony |
| 6,776,912 B2 | 8/2004 | Baurmeister |
| 6,796,955 B2 | 9/2004 | OMahony |
| 6,818,196 B2 | 11/2004 | Wong |
| 6,830,553 B1 | 12/2004 | Burbank et al. |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank et al. |
| 6,872,346 B2 | 3/2005 | Stillig |
| 6,878,283 B2 | 4/2005 | Thompson |
| 6,890,315 B1 | 5/2005 | Levin |
| 6,899,691 B2 | 5/2005 | Bainbridge |
| 6,923,782 B2 | 8/2005 | O'Mahony et al. |
| 6,948,697 B2 | 9/2005 | Herbert |
| 6,955,655 B2 | 10/2005 | Burbank et al. |
| 6,958,049 B1 | 10/2005 | Ash |
| 6,960,179 B2 | 11/2005 | Gura |
| 6,960,328 B2 | 11/2005 | Bortun et al. |
| 6,979,309 B2 | 12/2005 | Burbank et al. |
| 7,004,924 B1 | 2/2006 | Brugger et al. |
| 7,007,549 B2 | 3/2006 | Kwon |
| 7,033,498 B2 | 4/2006 | Wong |
| 7,040,142 B2 | 5/2006 | Burbank |
| 7,087,026 B2 | 8/2006 | Callister |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,270,015 B1 | 9/2007 | Feller |
| 7,273,465 B2 | 9/2007 | Ash |
| 7,276,042 B2 | 10/2007 | Polaschegg et al. |
| 7,300,413 B2 | 11/2007 | Burbank et al. |
| 7,309,323 B2 | 12/2007 | Gura et al. |
| 7,314,208 B1 | 1/2008 | Rightley |
| 7,317,967 B2 | 1/2008 | DiGianfilippo |
| 7,332,096 B2 | 2/2008 | Blickhan |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,351,218 B2 | 4/2008 | Bene |
| 7,387,022 B1 | 6/2008 | Korniyenko |
| 7,494,590 B2 | 2/2009 | Felding et al. |
| 7,531,098 B2 | 5/2009 | Robinson |
| 7,566,432 B2 | 7/2009 | Wong |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,736,507 B2 | 6/2010 | Wong |
| 7,755,488 B2 | 7/2010 | Dvorsky |
| 7,776,210 B2 | 8/2010 | Rosenbaum |
| 7,780,619 B2 | 8/2010 | Brugger |
| 7,794,141 B2 | 9/2010 | Perry |
| 7,873,489 B2 | 1/2011 | Dolgos |
| 7,874,999 B2 | 1/2011 | Busby |
| 7,886,611 B2 | 2/2011 | OMahony |
| 7,896,829 B2 | 3/2011 | Gura |
| 7,901,376 B2 | 3/2011 | Steck et al. |
| 7,922,898 B2 | 4/2011 | Jonsson |
| 7,922,899 B2 | 4/2011 | Vasta |

(56) References Cited

U.S. PATENT DOCUMENTS

| | | |
|---|---|---|
| 7,935,074 B2 | 5/2011 | Plahey |
| 7,959,129 B2 | 6/2011 | Matsumoto |
| 7,981,082 B2 | 7/2011 | Wang |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,161 B2 | 10/2011 | Gura |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,142,383 B2 | 3/2012 | Dannenmaier |
| 8,152,751 B2 | 4/2012 | Roger |
| 8,187,184 B2 | 5/2012 | Muller |
| 8,197,431 B2 | 6/2012 | Bennison |
| 8,221,320 B2 | 7/2012 | Bouton |
| 8,240,636 B2 | 8/2012 | Smith |
| 8,323,492 B2 | 12/2012 | Childers |
| 8,376,978 B2 | 2/2013 | Roger |
| 8,449,487 B2 | 5/2013 | Hovland |
| 8,696,626 B2 | 4/2014 | Kirsch |
| 2002/0068364 A1 | 6/2002 | Arai et al. |
| 2002/0085951 A1 | 7/2002 | Gelfand et al. |
| 2002/0112609 A1 | 8/2002 | Wong |
| 2002/0113016 A1 | 8/2002 | Takai |
| 2002/0147423 A1 | 10/2002 | Burbank |
| 2002/0158019 A1 | 10/2002 | Collins |
| 2002/0187069 A1 | 12/2002 | Levin |
| 2002/0193679 A1 | 12/2002 | Malave |
| 2003/0012905 A1 | 1/2003 | Zumbrum |
| 2003/0048185 A1 | 3/2003 | Citrenbaum |
| 2003/0056585 A1 | 3/2003 | Furuki |
| 2003/0113931 A1 | 6/2003 | Pan |
| 2003/0113932 A1 | 6/2003 | Sternberg |
| 2003/0128125 A1 | 7/2003 | Burbank |
| 2003/0216677 A1 | 11/2003 | Pan |
| 2003/0220598 A1 | 11/2003 | Busby |
| 2003/0220606 A1 | 11/2003 | Busby |
| 2003/0236482 A1 | 12/2003 | Gorsuch |
| 2004/0021108 A1 | 2/2004 | Hallback |
| 2004/0031756 A1 | 2/2004 | Suzuki |
| 2004/0167465 A1 | 8/2004 | Mihai |
| 2005/0070837 A1 | 3/2005 | Ferrarini et al. |
| 2005/0086008 A1 | 4/2005 | DiGianfilippo |
| 2005/0101901 A1 | 5/2005 | Gura |
| 2005/0131332 A1 | 6/2005 | Kelly et al. |
| 2005/0133439 A1 | 6/2005 | Blickhan |
| 2005/0150309 A1 | 7/2005 | Beard |
| 2005/0240233 A1 | 10/2005 | Lippert |
| 2006/0064053 A1 | 3/2006 | Bollish |
| 2006/0122552 A1 | 6/2006 | O'Mahony |
| 2006/0195064 A1 | 8/2006 | Plahey |
| 2006/0226057 A1 | 10/2006 | Robinson |
| 2006/0241543 A1 | 10/2006 | Gura |
| 2006/0289342 A1 | 12/2006 | Sugioka |
| 2007/0060786 A1 | 3/2007 | Gura |
| 2007/0112297 A1 | 5/2007 | Plahey et al. |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit et al. |
| 2007/0276328 A1 | 11/2007 | Childers |
| 2008/0006570 A1 | 1/2008 | Gura |
| 2008/0021366 A1 | 1/2008 | Gura |
| 2008/0041136 A1 | 2/2008 | Kopelman et al. |
| 2008/0041792 A1 | 2/2008 | Crnkovich et al. |
| 2008/0051689 A1 | 2/2008 | Gura |
| 2008/0058696 A1 | 3/2008 | Gura |
| 2008/0065006 A1 | 3/2008 | Roger |
| 2008/0149563 A1 | 6/2008 | Ash |
| 2008/0195021 A1 | 8/2008 | Roger |
| 2008/0195060 A1 | 8/2008 | Roger |
| 2008/0208103 A1 | 8/2008 | Demers |
| 2008/0217245 A1 | 9/2008 | Rambod |
| 2008/0230450 A1 | 9/2008 | Burbank et al. |
| 2008/0258735 A1 | 10/2008 | Quackenbush et al. |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0095679 A1 | 4/2009 | Demers et al. |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0107902 A1 | 4/2009 | Childers |
| 2009/0112507 A1 | 4/2009 | Edney |
| 2009/0113335 A1 | 4/2009 | Sandoe et al. |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0173682 A1 | 7/2009 | Robinson |
| 2009/0282980 A1 | 11/2009 | Gura |
| 2009/0312694 A1 | 12/2009 | Bedingfield et al. |
| 2010/0022936 A1 | 1/2010 | Gura |
| 2010/0078381 A1 | 4/2010 | Merchant |
| 2010/0078387 A1 | 4/2010 | Wong |
| 2010/0084330 A1 | 4/2010 | Wong |
| 2010/0094193 A1 | 4/2010 | Gura |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0179464 A1 | 7/2010 | Smith |
| 2010/0184198 A1 | 7/2010 | Joseph |
| 2010/0209300 A1 | 8/2010 | Dirac |
| 2010/0312161 A1 | 12/2010 | Jonsson |
| 2010/0326911 A1 | 12/2010 | Rosenbaum |
| 2010/0326916 A1 | 12/2010 | Wrazel |
| 2011/0000830 A1 | 1/2011 | Ikeda |
| 2011/0000832 A1 | 1/2011 | Kelly et al. |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0071465 A1 | 3/2011 | Wang |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanski |
| 2011/0107251 A1 | 5/2011 | Guaitoli |
| 2011/0108482 A1 | 5/2011 | Lovell |
| 2011/0125073 A1 | 5/2011 | Rambod |

(56) References Cited

U.S. PATENT DOCUMENTS

| | | |
|---|---|---|
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |
| 2013/0199998 A1 | 8/2013 | Kelly |
| 2013/0220907 A1 | 8/2013 | Fulkerson |

FOREIGN PATENT DOCUMENTS

| | | |
|---|---|---|
| EP | 0808633 | 11/1997 |
| EP | 2237814 | 10/2010 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 U | 7/1985 |
| JP | H02114269 U | 9/1990 |
| JP | H0413143 U | 2/1992 |
| JP | H05172268 A | 9/1993 |
| JP | 2002119585 A | 4/2002 |
| JP | 2002523772 | 7/2002 |
| JP | 2003502091 | 1/2003 |
| JP | 2004057284 | 2/2004 |
| JP | 2008291911 A | 4/2008 |
| JP | 2009521965 | 6/2009 |
| WO | 8002806 | 12/1980 |
| WO | 9625214 | 8/1996 |
| WO | 9727490 | 7/1997 |
| WO | 9823353 | 6/1998 |
| WO | 2005089832 | 9/2005 |
| WO | 2005089832 A2 | 9/2005 |
| WO | 2006120415 | 11/2006 |
| WO | 2007028056 | 3/2007 |
| WO | 2009045589 | 4/2009 |
| WO | 2009045589 A2 | 4/2009 |
| WO | 2009073567 | 6/2009 |
| WO | 2009091963 | 7/2009 |
| WO | 2009157877 | 12/2009 |
| WO | 2010042666 | 4/2010 |
| WO | 2010042667 | 4/2010 |
| WO | 2010062698 | 6/2010 |
| WO | 2010081121 | 7/2010 |
| WO | 2010114932 | 7/2010 |
| WO | 2012108910 | 8/2012 |
| WO | 2014105755 | 7/2014 |

OTHER PUBLICATIONS

Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual Model 1500, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Reyes et al., "Acid-Base Derangements During Sorbent Regenerative Hemodialysis in Mechanically Ventilated Patients", Critical Care Medicine, vol. 19, No. 4, 1991, 554-559 (col. 2, lines 17-22).
Cobe Renal Care, Inc., "Sorbent Dialysis Primer", Edition 4, Sep. 1993.
Cobe Laboratories, Inc., 'CentrySystem 3 Dialysis Control Unit Operators Manual', Sep. 1988.
Fresenius USA, Inc., "Fresenius 2008H Hemodialysis Machine", Part No. 490005, Revision H, 1994-2001.
Renal Solutions, Inc., 510(K) for the SORB+ and HISORB+ Cartridges, Mar. 31, 2003.
CD Medical, Inc., "Operator's Manual Drake Willock 480 Ultrafiltration Control Single Patient Delivery System", 1988.
Renal Solutions, Inc., 'Dialysate Tubing Set and Dialysate Reservoir Bag for the Allient Sorbent Hemodialysis System', Instructions, 2004.
NxStage Medical, Inc., "NxStage System One User's Guide", Software Version 4.3, Part 1 through Part 6-20, 2006.
NxStage Medical, Inc., "NxStage System One User's Guide", Software Version 4.3, Part 6-20 through Part C-17, 2006.
Manns et al., "The acu-men: A New Device for Continuous Renal Replacement Therapy in Acute Renal Failure", Kidney International, vol. 54 (1998), 268-274.
Redy 2000 Operator's Manual (1991) (Sorbent cartridge-based hemodialysis system).
Redy 2000 Service Manual (1989) (Sorbent cartridge-based hemodialysis system).
Seratron Dialysis Control System Operations Manual (cumulative 1980).
Ward et al., 'Sorbent Dialysis Regenerated Dialysis Delivery Systems', Peritoneal Dialysis Bulletin, Chapter 8, 3(2): S41-S48 (Apr.-Jun. 1983).
Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
Fresenius AG, 'Acumen Acute Dialysis Machine Operating Instructions', Version 1.0, May 1996.

(56) References Cited

OTHER PUBLICATIONS

Renal Solutions, Special 510(k) Device Modification, Allient Sorbent Hemodialysis System, Mar. 15, 2007.
International Search Report PCT/US08/85062, Mar. 20, 2009, XCorporeal, Inc.
International Search Report for PCT/US09/59906, Xcorporeal, Inc., May 8, 2012.
International Search Report for PCT/US09/62840, Xcorporeal, Inc. Feb. 10, 2012.
International Search Report for PCT/US11/53184, Xcorporeal, Inc., Mar. 2, 2012.
International Search Report for PCT/US09/31228, Xcorporeal, Inc., Jun. 19, 2009.
International Search Report for PCT/US09/59907, Xcorporeal, Inc., Apr. 13, 2010.
International Search Report for PCT/US10/29500, Xcorporeal, Inc., Jul. 2, 2010.
Examination Report for PCT/US09/59906, New Zealand Intellectual Property Office, May 15, 2012.
Examination Report for PCT/US08/85062, Mexican Patent Office, Mar. 11, 2013.
Search report for PCT/US10/20698, Jul. 15, 2010, XCorporeal, Inc.
International Search Report for PCT/US10/20698, Xcorporeal, Inc., Jun. 16, 2010.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 1-3.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
International Preliminary Report on Patentability for PCT/US2009/059907, Apr. 15, 2010, Fresenius Medical Care Holdings, Inc.
International Search Report for PCT/US2009/059907, Apr. 15, 2010, Fresenius Medical Care Holdings, Inc.
International Search Report for PCT/US08/85062, Jun. 11, 2009, XCorporeal, Inc.
International Search Report for PCT/US10/29500, Jul. 20, 2010, XCorporeal, Inc.
International Search Report for PCT/US13/77234, Jun. 9, 2014.
First Office Action for Canadian Application No. CA2706919, dated Jan. 20, 2015.
Office Action dated Jan. 27, 2015 for US Appl. No. 13/372,202.
European Search Report for Application No. EP20090829649, dated Jan. 22, 2015.

MANIFOLDS FOR USE IN CONDUCTING DIALYSIS

CROSS-REFERENCE

The present application is a continuation of U.S. patent application Ser. No. 12/237,914, filed on Sep. 25, 2008, now U.S. Pat. No. 8,105,487 which calls priority to U.S. Patent Provisional Application No. 60/975,157 filed on Sep. 25, 2007.

FIELD

The present application relates generally to the field of blood purification systems and methods. More specifically, the present invention relates to novel methods and systems for conducting hemofiltration and hemodialysis.

BACKGROUND

Blood purification systems, which are used for conducting hemodialysis, hemodiafiltration or hemofiltration, involve the extracorporeal circulation of blood through an exchanger having a semi permeable membrane. Such systems further include a hydraulic system for circulating blood and a hydraulic system for circulating replacement fluid or dialysate comprising the main electrolytes of the blood in concentrations close to those in the blood of a healthy subject. Most of the conventionally available blood purification systems are, however, quite bulky in size and difficult to operate. Further, the design of these systems makes them unwieldy and not conducive to the use and installation of disposable components.

The conventional design of prior art hemodiafiltration systems employs single pass systems. In single pass systems, the dialysate passes by the blood in the dialyzer one time and then is disposed. Single pass systems are fraught with a plurality of disadvantages, arising from the use of large amounts of water:

- Assuming a 50% rejection rate by the R.O. (Reverse Osmosis) system, at least 1000 to 1500 ml/min of water is required.
- A water purification system for providing a continuous flow of 100 to 800 ml/minute of purified water is required.
- An electrical circuit of at least 15 amps is required, in order to pump 100 to 800 ml of water/minute, and
- A floor drain or any other reservoir capable of accommodating at least 1500 ml/min of used dialysate and RO rejection water.

U.S. Pat. No. 4,469,593 to Ishihara, et al discloses "a blood purification apparatus [that] includes an extracorporeal circulation system, a blood purifier provided in the system for purifying blood by dialysis or filtration through a semi permeable membrane, a circulation blood volume measuring instrument for measuring changes in a circulating blood volume within a patient's body, a control section comprising a memory for storing a program for a pattern of changes in the circulating blood volume during blood purification, the program being matched to the condition of a patient, and a regulator connected to the extracorporeal circulation system and the control section, for controlling the circulating blood volume, the regulator being controlled by the control section on the basis of the circulating blood volume measured during blood purification and the programmed amount. In this apparatus, optimum blood purification is carried out while maintaining the circulating blood volume at a prescribed level."

U.S. Pat. No. 5,114,580 to Ahmad, et al discloses "[a] hemodialysis system that has a blood circuit and a hemofiltrate circuit interconnected at a hemofilter and an air collection chamber. If an infusion of sterile fluid to the returning blood is needed during the dialysis treatment, filtrate in the filtrate circuit is pumped back into the blood circuit. This is also done to purge the blood circuit of blood and return it to the patient at the conclusion of a dialysis treatment. A blood pump in the blood circuit incorporates a flexible vessel in conjunction with pinch valves which self expand in a controlled manner from a compressed condition to fill with blood from the patient in a suction stroke controlled by the patient's blood delivery rate. Compression of the vessel by an external member then forces the blood through the rest of the blood circuit."

U.S. Pat. No. 6,303,036 to Collins, et al discloses "[a]n apparatus and method for hemodiafiltration . . . [that] includes a first dialyzer cartridge containing a semi-permeable membrane that divides the dialyzer into a blood compartment and a dialysate compartment. Fluid discharged from the blood compartment of the first dialyzer cartridge is mixed with sterile substitution fluid to form a fluid mixture and the mixture enters a second dialyzer cartridge. The second dialyzer cartridge contains a second semi-permeable membrane which divides the second dialyzer cartridge into a blood compartment and a dialysate compartment. Hemodiafiltration occurs in both cartridges."

None of these systems, however, address the aforementioned disadvantages of prior art blood purification systems. Conventional systems are also less reliable because of the necessity of using a myriad of tubes comprising the fluid circuits of the purification systems, thus increasing the risks of leakage and breakage.

Further, conventional blood purification systems do not have built-in functionality to check the integrity and authenticity of the disposables employed in the system. Still further, conventional systems lack the capability to allow the user of the system to interact with a remote patient care facility.

Accordingly, there is a need for a multiple-pass sorbent-based hemodiafiltration system that lowers the overall water requirements relative to conventional systems. There is also a need for a novel manifold that can be used in a single pass sorbent-based hemodiafiltration system as well as in the multiple-pass system of the present invention, which offers a lightweight structure with molded blood and dialysate flow paths to avoid a complicated mesh of tubing. It is also desirable that the novel manifold has integrated blood purification system components, such as sensors, pumps and disposables, thus enhancing fail-safe functioning of a patient's blood treatment.

SUMMARY

The present application discloses novel systems for conducting the filtration of blood using manifolds. In one embodiment, the manifold comprises a first flow path formed in a plastic substrate comprising a plurality of sensors integrated therein and tubing that receives blood from a first inlet port and passes blood to a dialyzer; a component space formed in the plastic substrate for receiving a dialyzer; a second flow path formed in the plastic substrate comprising at least one blood leak sensor integrated therein and tubing that receives a first fluid from a dialyzer and passes the first fluid to a first outlet port and a second outlet port, wherein the first outlet port is in fluid communication with a collection reservoir and the second outlet port is in fluid communication with a dialysate regeneration system; a third flow path formed in the plastic substrate comprising tubing that receives a second fluid from a second inlet port and passes the second fluid to the dialyzer; and a fourth flow path formed in the plastic substrate comprising at least one sensor and tubing that receives purified blood from the dialyzer and passes the purified blood to a third outlet port.

Optionally, a pump, such as a peristaltic pump, is in fluid communication with the first flow path. The sensors integrated into the first flow path are at least one of a pressure transducer and a flow meter. The transducers are directly molded into the manifold and are made of synthetic rubber. A flow meter is integrated into the second flow path. At least two pumps are in fluid communication with the second flow path. The fourth flow path further comprises tubing for receiving fluid from a third inlet port. The third inlet port is connected to a substitution fluid container.

In another embodiment, the present application discloses a manifold for conducting filtration of blood comprising a first inlet port, a first flow path formed in a plastic substrate comprising a plurality of sensors integrated therein wherein the first flow path forms a pathway for transporting blood from the first inlet port and to a component space formed in the plastic substrate, a second flow path formed in the plastic substrate comprising at least one blood leak sensor integrated therein wherein the second flow path forms a pathway for transporting a first fluid from the component space to a first outlet port and a second outlet port, a third flow path formed in the plastic substrate comprising tubing wherein the third flow path forms a pathway for transporting a second fluid from a second inlet port to the component space, and a fourth flow path formed in the plastic substrate comprising at least one sensor, wherein the fourth flow path forms a pathway for transporting purified blood from the component space to a third outlet port.

In another embodiment, the present application discloses a system for conducting ultrafiltration having a manifold comprising a first flow path formed in a plastic substrate comprising a plurality of sensors integrated therein and tubing that passes blood to a first outlet port, wherein the first outlet port is in fluid communication with a first pump external to the manifold, receives blood from a first inlet port, wherein the first inlet port is in fluid communication with the first pump, and passes the blood to a dialyzer; a component space formed in the plastic substrate for receiving a dialyzer; a second flow path formed in the plastic substrate comprising at least one sensor integrated therein and tubing that receives a first fluid from the dialyzer and passes the first fluid to a second outlet port, wherein second outlet port is in fluid communication with a second pump; and a third flow path formed in the plastic substrate comprising at least one sensor and tubing that receives the first fluid from a second inlet port, wherein the second inlet port is in fluid communication with the second pump, and passes said first fluid to a third outlet port.

Optionally, the first flow path comprises at least two pressure sensors. The at least one sensor of the third flow path is a blood leak sensor. The system further comprises a fourth flow path formed in the substrate comprising at least one sensor and tubing that receives a second fluid from said dialyzer and passes said second fluid to a fourth outlet port. The at least one sensor in the fourth flow path is an air detector. The third flow path further comprises a flow meter. The at least one sensor in the second flow path is a pressure sensor. The system further comprises a housing for containing the first pump, said second pump, and the manifold.

In another embodiment, the present application discloses a manifold for conducting ultrafiltration comprising a first flow path formed in a plastic substrate comprising at least one sensor integrated therein wherein the first flow path forms a pathway for passing blood from a first inlet port to a component space, a component space formed in the plastic substrate, a second flow path formed in the plastic substrate comprising at least one sensor integrated therein wherein the second flow path forms a pathway for passing a first fluid from the component space to a second outlet port; and a third flow path formed in the plastic substrate comprising at least one blood leak sensor and flow meter, wherein the third flow path forms a pathway for passing said first fluid from a second inlet port to a third outlet port.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1A:
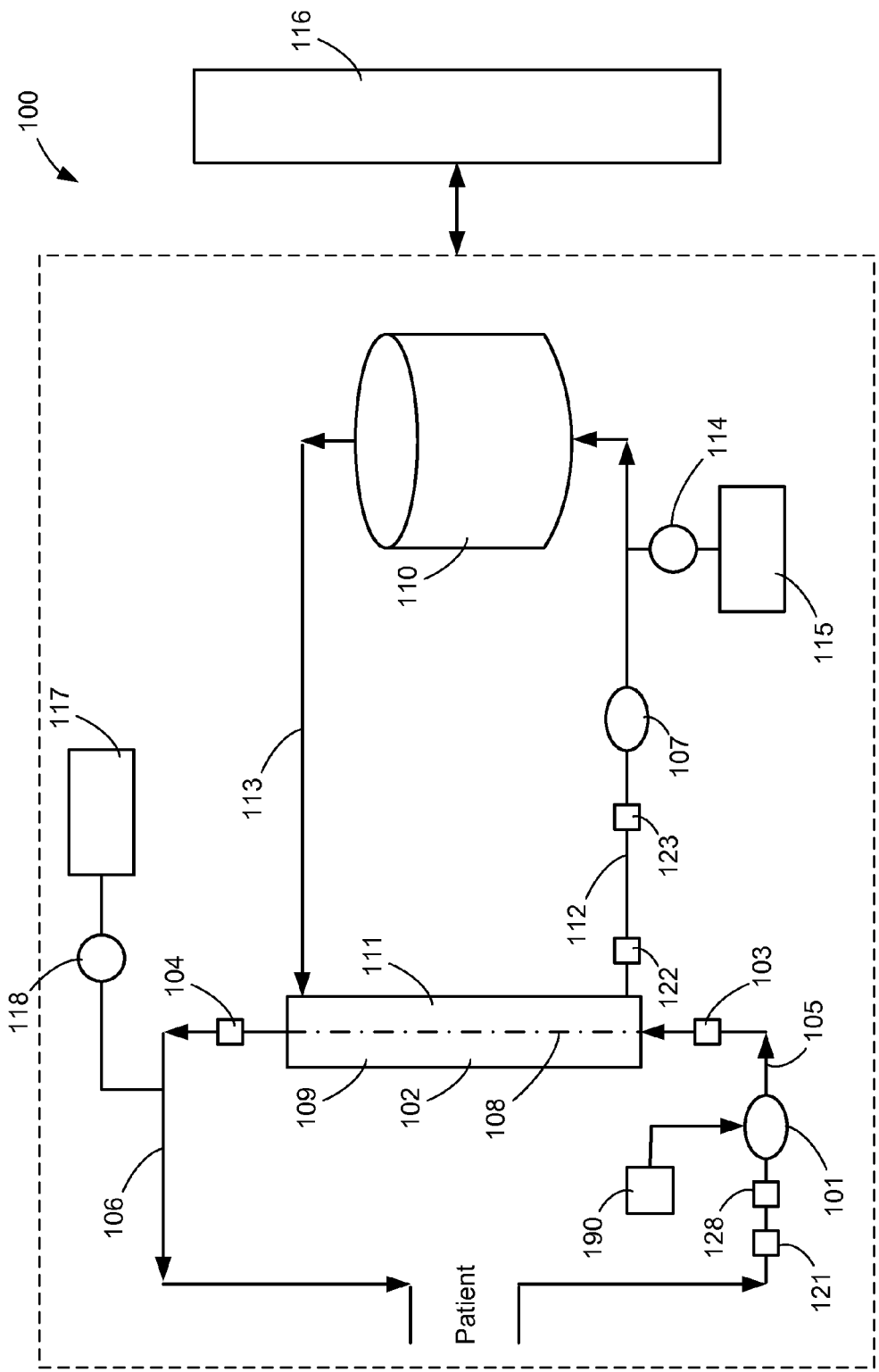
FIG. 1a is a functional block diagram of one embodiment of a multiple-pass sorbent-based hemodiafiltration system of the present invention.

The present application discloses a plurality of novel embodiments which can be practiced independently or in novel combination with each other.

In one embodiment, the present application discloses a multiple-pass, sorbent-based hemodiafiltration system, advantageously combining hemofiltration and hemodialysis in a multiple pass configuration.

In another embodiment, the present application discloses novel manifold supports for blood purification systems, such as, but not limited to hemodiafiltration and ultrafiltration. In one embodiment, the novel manifold of the present invention comprises a composite plastic manifold, into which the blood and dialysate flow paths are molded. This plastic based manifold can be used with the multiple-pass sorbent-based hemodiafiltration system of the present invention.

In another embodiment, blood purification system components, such as sensors, pumps, and disposables are integrated into the molded novel manifold. Preferably, disposable items such as but not limited to dialyzer and sorbent cartridges, are detachably loadable on to the manifold. In one embodiment, sensors, such as but not limited to those for pressure and air monitoring and blood leak detection are also integrated with the manifold. In another embodiment, blood circuit pumps are integrated with the manifold. In another embodiment, the valve membranes are integrated with the manifold.

In yet another embodiment, an ultrafiltration system is integrated into a novel manifold by molding both blood and ultrafiltrate flow paths in the manifold. In one embodiment, a hemofilter cartridge is placed into the manifold so that it can be removed and replaced.

In one embodiment, the manifolds disclosed herein comprise single, composite plastic structures, also referred to as substrates or housings, that can be made by combining two plastic substrate halves.

In another embodiment, the present application discloses a dialysis system that supports an electronic-based lockout system. Accordingly, in one embodiment, a reader is mounted on the system housing(s) and/or manifold(s), such as but not limited to the hemodiafiltration and ultrafiltration manifolds, and reads identification indicia on disposable items that are loaded onto the dialysis housing(s) and/or manifolds. The reader communicates with a database over a network, such as a public network or private network, to check if the disposable items are valid, accurate, or of sufficient integrity to be safe and ready for use. This is done by querying information on the disposable items from the remote database, based on the identification indicia of the items. If the disposable item has an "invalid" or "compromised" status, (based on the information received from the database) the .system "locks out" the use of the loaded disposable, and thus does not allow the user to proceed with using the system for treatment.

Reference will now be made to specific embodiments of the present invention. The present invention is directed toward multiple embodiments. Language used in this specification should not be interpreted as a general disavowal of any one specific embodiment or used to limit the claims beyond the meaning of the terms used therein.

FIG. 1a is a functional block diagram of one embodiment of a multiple-pass sorbent-based hemodiafiltration system of the present invention. In one embodiment, hemodiafiltration system 100 employs a dialyzer cartridge comprising a high flux membrane to remove toxins from the blood both by diffusion and by convection. The removal of toxins by diffusion is accomplished by establishing a concentration gradient across the semi-permeable membrane by allowing a dialysate solution to flow on one side of the membrane in one direction while simultaneously allowing blood to flow on the other side of the membrane in opposite direction. To enhance removal of toxins using hemodiafiltration, a substitution fluid is continuously added to the blood either prior to the dialyzer cartridge (pre-dilution) or after the dialyzer cartridge (post-dilution). An amount of fluid equal to that of the added substitution fluid is "ultra-filtered" across the dialyzer cartridge membrane, carrying the added solutes with it.

Now referring to FIG. 1a, in one embodiment, the blood containing toxins is pumped from a blood vessel of a patient by a blood pump 101 and is transferred to flow through dialyzer cartridge 102. Optionally, inlet and outlet pressure sensors 103, 104 in the blood circuit measure the pressure of blood both before it enters the dialyzer cartridge 102 at the blood inlet tube 105 and after leaving the dialyzer cartridge 102 at the blood outlet tube 106. Pressure readings from sensors 103, 104, 128 are used as a monitoring and control parameter of the blood flow. An ultrasonic flow meter 121 may be interposed in the portion of blood inlet tube 105 that is located directly upstream from the blood pump 101. The ultrasonic flow meter 121 is positioned to monitor and maintain a predetermined rate of flow of blood in the impure blood supply line. A substitution fluid 190 may be continuously added to the blood either prior to the dialyzer cartridge (pre-dilution) or after the dialyzer cartridge (post-dilution).

Figure 1B:
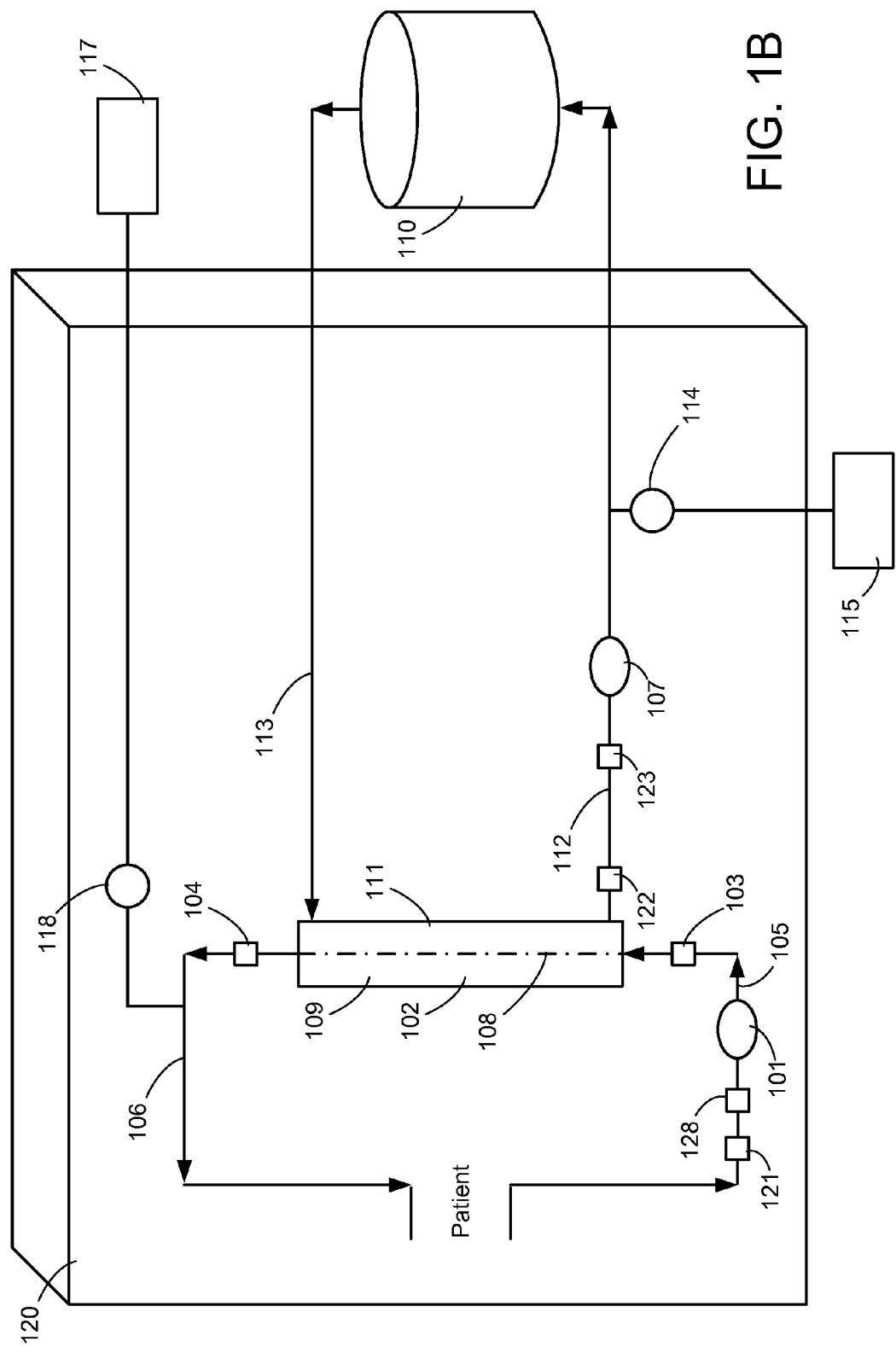
FIG. 1b is an illustration of one embodiment of a hemodiafiltration manifold of the present invention.

In one embodiment, as shown in FIGS. 1a and 1b, dialyzer cartridge 102 comprises a semi-permeable membrane 108 that divides the dialyzer 102 into a blood chamber 109 and a dialysate chamber 111. As blood passes through the blood chamber 109, uremic toxins are filtered across the semi-permeable membrane 108 on account of convection. Additional blood toxins are transferred across the semi-permeable membrane 108 by diffusion, primarily induced by a difference in concentration of the fluids flowing through the blood and dialysate chambers 109, 111 respectively. The dialyzer cartridge used may be of any type suitable for hemodialysis, hemodiafiltration, hemofiltration, or hemoconcentration, as are known in the art. In one embodiment, the dialyzer 102 contains a high flux membrane. Examples of suitable dialyzer cartridges include, but are not limited to, Fresenius® F60, F80 available from Fresenius Medical Care of Lexington, Mass., Baxter CT 110, CT 190, Syntra® 160 available from Baxter of Deerfield, Ill., or Minntech Hemocor HPH® 1000, Primus® 1350, 2000 available from Minntech of Minneapolis, Minn.

In one embodiment of the present invention, dialysate pump 107 draws spent dialysate from the dialyzer cartridge 102 and forces the dialysate into a dialysate regeneration system 110 and back into the dialyzer cartridge 102 in a multiple pass loop, thus generating "re-generated" or fresh dialysate. Optionally, a flow meter 122 is interposed in the spent dialysate supply tube 112 upstream from dialysate pump 107, which monitors and maintains a predetermined rate of flow of dialysate. A blood leak sensor 123 is also interposed in spent dialysate supply tube 112.

The multi-pass dialysate regeneration system 110 of the present invention comprises a plurality of cartridges and/or filters containing sorbents for regenerating the spent dialysate. By regenerating the dialysate with sorbent cartridges, the hemodiafiltration system 100 of the present invention requires only a small fraction of the amount of dialysate of a conventional single-pass hemodialysis device. In one embodiment, each sorbent cartridge in the dialysate regeneration system 110 is a miniaturized cartridge containing a distinct sorbent. For example, the dialysate regeneration system may employ five sorbent cartridges, wherein each cartridge separately contains activated charcoal, urease, zirconium phosphate, hydrous zirconium oxide and activated carbon. In another embodiment each cartridge may comprise a plurality of layers of sorbents described above and there may be a plurality of such separate layered cartridges connected to each other in series or parallel in the dialysate regeneration system. Persons of ordinary skill in the art would appreciate that activated charcoal, urease, zirconium phosphate, hydrous zirconium oxide and activated carbon are not the only chemicals that could be used as sorbents in the present invention. In fact, any number of additional or alternative sorbents, including polymer-based sorbents, could be employed without departing from the scope of the present invention.

The sorbent-based multiple-pass hemodiafiltration system of the present invention provides a plurality of advantages over conventional single-pass systems. These include:

No requirement of a continuous water source, a separate water purification machine or a floor drain as the system of present invention continuously regenerates a certain volume of dialysate. This allows for enhanced portability.

The present system requires low amperage electrical source, such as 15 amps, because the system recycles the same small volume of dialysate throughout the diafiltration procedure. Therefore, extra dialysate pumps, concentrate pumps and large heaters used for large volumes of dialysate in single pass dialysis systems are not required.

The present system can use low volumes of tap water, in the range of 6 liters, from which dialysate can be prepared for an entire treatment.

The sorbent system uses sorbent cartridges that act both as a water purifier and as a means to regenerate used dialysate into fresh dialysate.

While the current embodiment has separate pumps 101, 107 for pumping blood and dialysate through the dialyzer, in an alternate embodiment, a single dual-channel pulsatile pump that propels both blood and dialysate through the hemodiafiltration system 100 may be employed. Additionally, centrifugal, gear, or bladder pumps may be used.

In one embodiment, excess fluid waste is removed from the spent dialysate in the spent dialysate tube 112 using a volumetric waste micro-pump 114 and is deposited into a waste collection reservoir 115, which can be periodically emptied via an outlet such as a tap. An electronic control unit 116 comprising a microprocessor monitors and controls the functionality of all components of the system 100.

In one embodiment, dia-filtered blood exiting dialyzer cartridge 102 is mixed with regulated volumes of sterile substitution fluid that is pumped into the blood outlet tube 106 from a substitution fluid container 117 via a volumetric micropump 118. Substitution fluid is typically available as a sterile/non-pyrogenic fluid contained in flexible bags. This fluid may also be produced on-line by filtration of a non-sterile dialysate through a suitable filter cartridge rendering it sterile and non-pyrogenic.

FIG. 1b is an illustration of one embodiment of a hemodiafiltration manifold of the present invention. In one embodiment, hemodiafiltration manifold 120 comprises the blood and dialysate flow paths shown in the hemodialfiltration system 100 shown in FIG. 1a. As shown in FIG. 1b, the blood and dialysate flow paths are molded in a single compact plastic unit. Fluid flows in and out of the manifold at defined inlet and outlet ports, such as to and from a patient, to a waste reservoir, to a dialysate regeneration system, or from a substitution fluid reservoir. The sensors, such as dialyzer blood inlet pressure transducers 103, 128 and blood outlet pressure transducer 104; flow meters 121, 122; blood leak sensor 123; disposable sorbent cartridges of the dialysate regeneration system 110, which is external to the manifold; and volumetric pumps 101, 107, 114 and 118 are all integrated into the molding of the manifold 120. The disposable dialyzer 102 is directly integrated with the corresponding space in the manifold 120 to complete the blood and dialysate circuits, as shown in FIG. 1b. Preferably, pressure transducers 103, 104 are directly molded into the manifold with a multi-shot plastic injection molding process which reduces the need for manual assembly of these components. In one embodiment, the diaphragm of the transducers are made of synthetic rubber, such as polyisoprene, and co-molded into the ABS plastic substrate. Collection reservoir 115 and substitution fluid container 117 are also external to the manifold 120.

Figure 3:
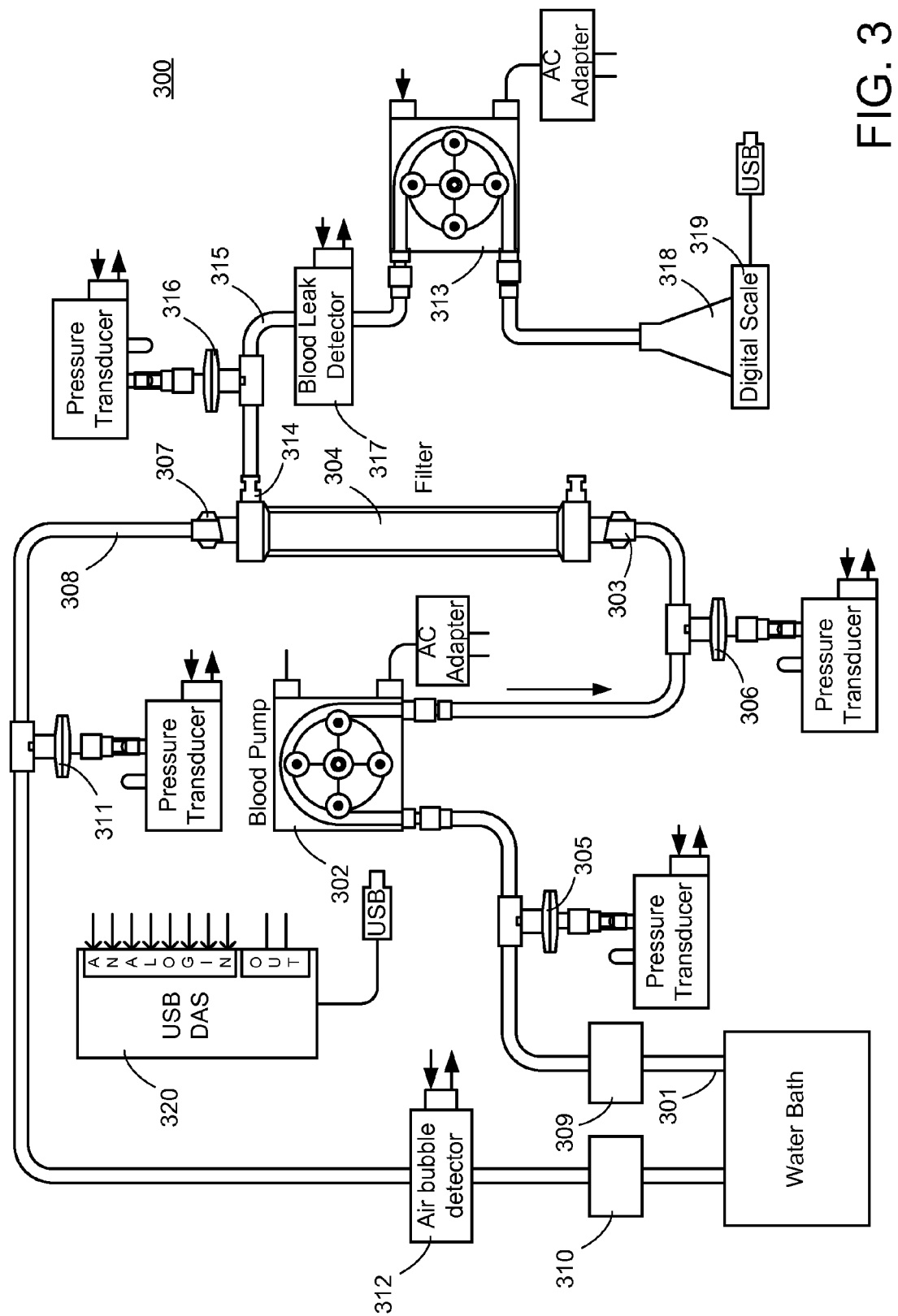
FIG. 3 is a functional block diagram showing one embodiment of an ultrafiltration treatment system of the present invention.

FIG. 3 is a functional block diagram showing one embodiment of an ultrafiltration treatment system 300 of the present invention. As shown in FIG. 3, blood from a patient is drawn into blood inlet tubing 301 by a pump, such as a peristaltic blood pump, 302 that forces the blood into a hemofilter cartridge 304 via blood inlet port 303. Inlet and outlet pressure transducers 305, 306 are connected in-line just before and after the blood pump 302. The hemofilter 304 comprises a semi-permeable membrane that allows excess fluid to be ultrafiltrated from the blood passing therethrough, by convection. Ultrafiltered blood is further pumped out of the hemofilter 304 through blood outlet port 307 into blood outlet tubing 308 for infusion back to into the patient. Regulators, such as clamps, 309, 310 are used in tubing 301 and 308 to regulate fluid flow therethrough.

A pressure transducer 311 is connected near the blood outlet port 307 followed by an air bubble detector 312 downstream from the pressure transducer 311. An ultrafiltrate pump, such as a peristaltic pump, 313 draws the ultrafiltrate waste from the hemofilter 304 via UF (ultrafiltrate) outlet port 314 and into the UF outlet tubing 315. A pressure transducer 316 and a blood leak detector 317 are transposed into the UF outlet tubing 315. Ultrafiltrate waste is finally pumped into a waste collection reservoir 318 such as a flask or soft bag, attached to the leg of an ambulatory patient and equipped with a drain port to allow intermittent emptying. The amount of ultrafiltrate waste generated can be monitored using any measurement technique, including a scale or flow meter. The microcontroller monitors and manages the functioning of the blood and UF pumps, pressure sensors as well as air and blood leak detectors. Standard luer connections such as luer slips and luer locks are used for connecting tubing to the pumps, the hemofilter and to the patient.

Figure 2A:
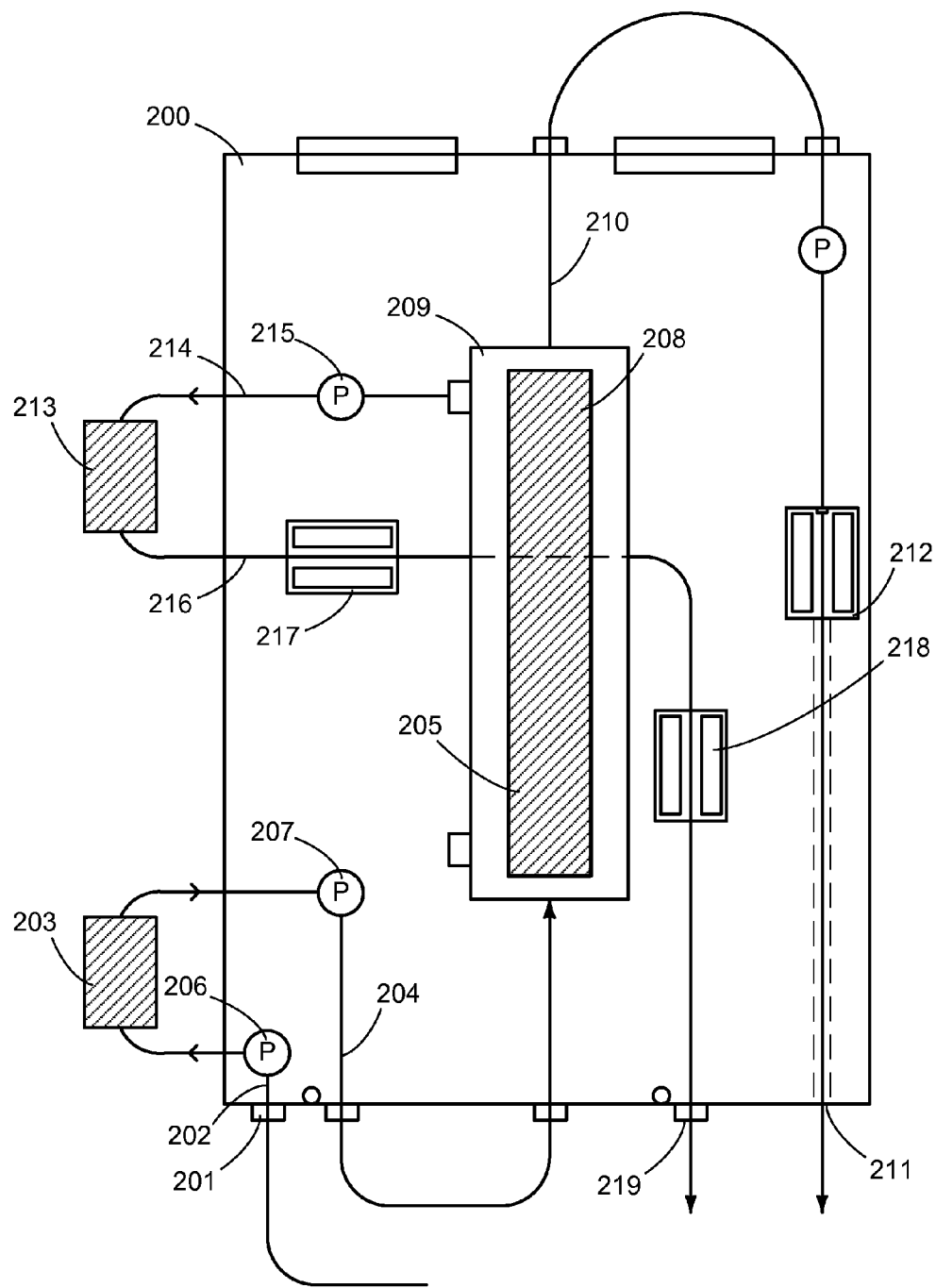
FIGS. 2a and 2b are a functional diagram and an illustration, respectively, of one embodiment of an ultrafiltration manifold used to support an ultrafiltration treatment system.
Figure 2B:
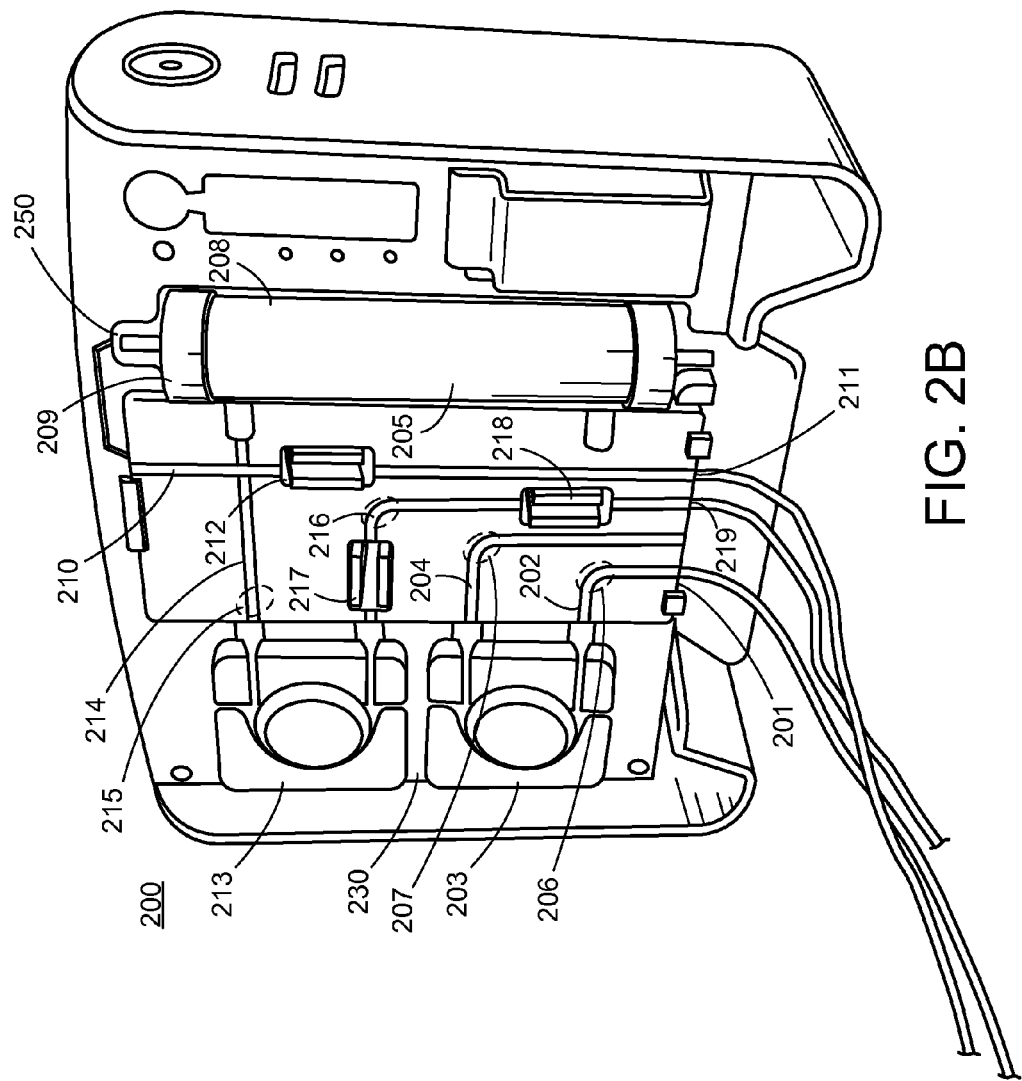

FIGS. 2a and 2b are a functional diagrams and an illustration, respectively, of one embodiment of an ultrafiltration manifold 200 used to support an ultrafiltration treatment system. In one embodiment, the ultrafiltration manifold 200 is an easy to assemble compact plastic unit that has built-in molded blood and waste flow paths. Optionally, the sensors, pumps and hemofilter cartridges can also be integrated with the compact plastic unit by insertion into concave moldings in the unit. In one embodiment, the ultrafiltration system of the present invention is capable of operating more than 8 hours per treatment and for up to 72 hours continuously. It should be appreciated that fluid flows in and out of the manifold through defined inlet and outlet ports, such as to and from external pumps, to a waste UF reservoir, or to a patient return line.

Figure 2C:
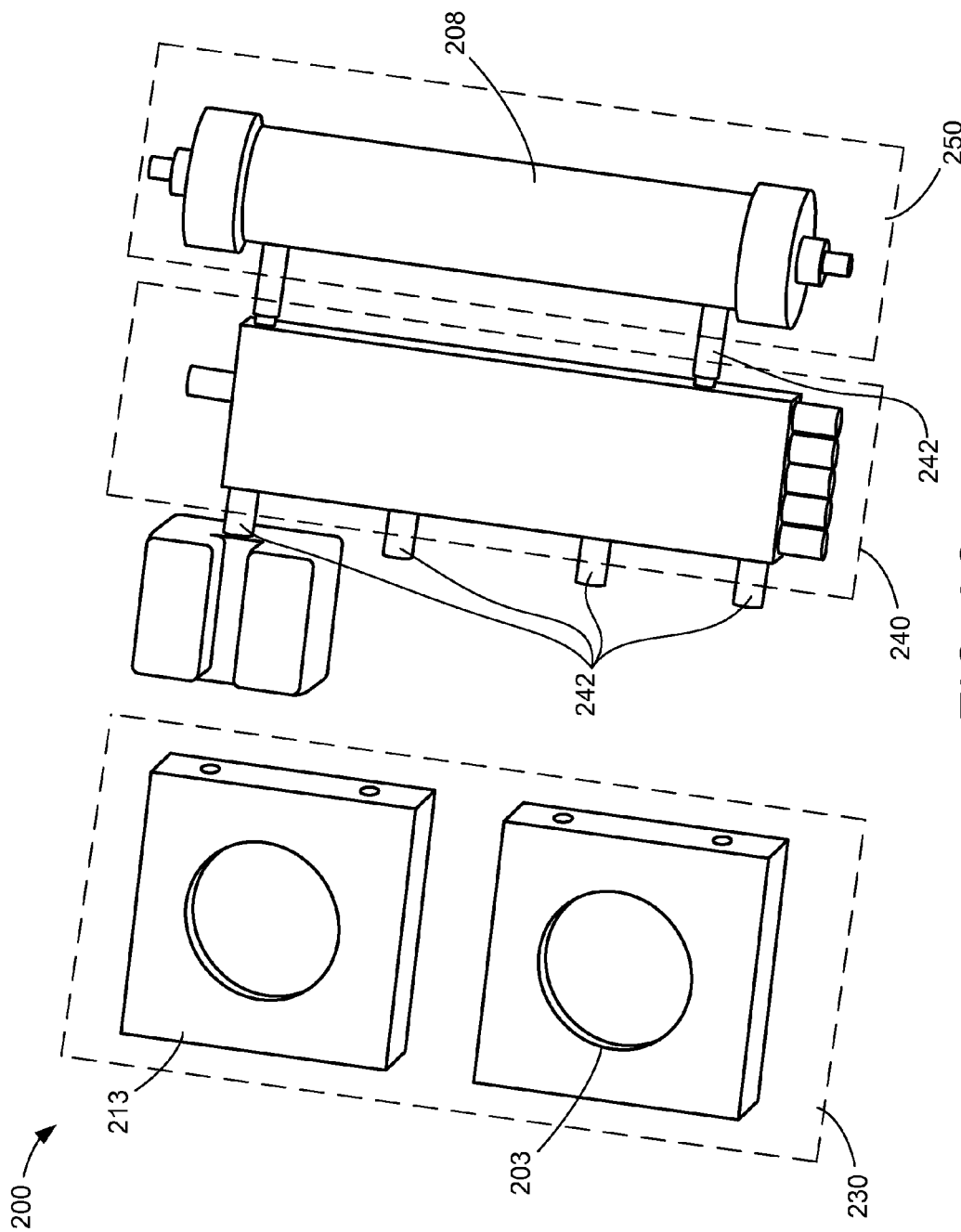
FIG. 2c shows a modular assembly of an ultrafiltration manifold in one embodiment of the present invention.

FIG. 2c shows a modular assembly of an ultrafiltration manifold in one embodiment of the present invention. As shown in FIG. 2c, the housing 290 comprises blood and waste pumps 203, 213 respectively in a pumping section 230; a module 240 comprises molded flow paths for blood and ultrafiltrate wastes and a hemofilter module 250 comprising a hemofilter cartridge 208. This modular design allows quick and easy assembly of various modules into a single compact structure 290.

Figure 2D:
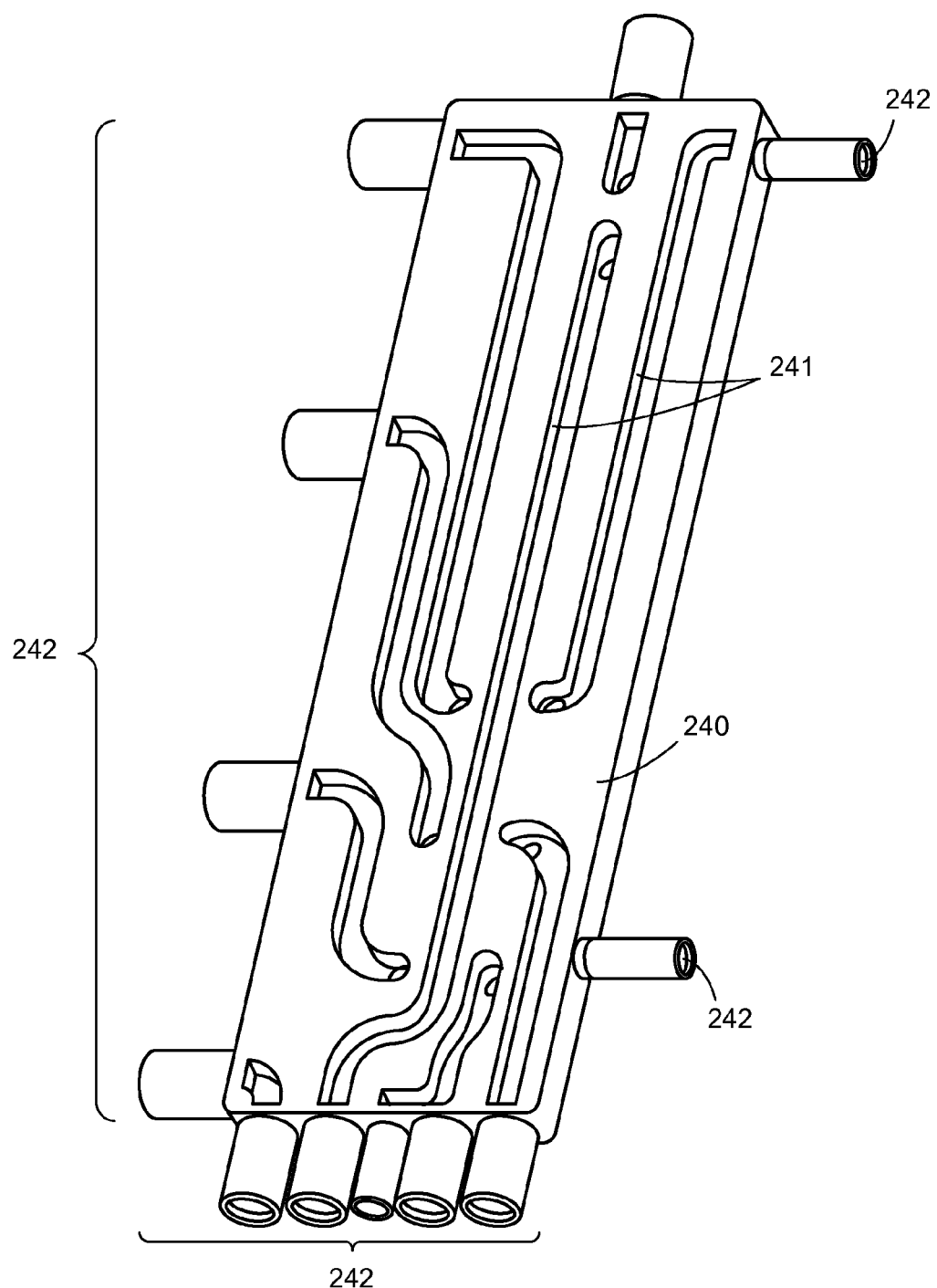
FIG. 2d shows a larger view of a mid-body module in one embodiment of the ultrafiltration manifold of the present invention.

FIG. 2d shows an enlarged view of a mid-body module 240 in one embodiment of the ultrafiltration manifold of the present invention. In one embodiment, mid-body module 240 comprises built-in molded flow paths 241 for carrying blood and waste. Connection ports 242 are also molded into the mid-body module for connecting (via luer connectors and tubing) to pumps at one end of mid-body module 240 and to a hemofilter cartridge at the other end of mid-body module 240.

Referring back to FIGS. 2a and 2b simultaneously, blood is drawn into the manifold 200 via blood inlet port 201 and molded flow path 202 using a blood volumetric pump 203. Blood volumetric pump 203 pumps blood into hemofilter cartridge 208 via the molded flow path 204. Inlet pressure sensors 206, 207 are also integrated into manifold 200 in molded flow paths 202, 204.

In one embodiment the hemofilter cartridge 208 comprises a hollow tube further comprising a plurality of hollow fiber tubes whose walls act as a semi-permeable membrane. The plurality of semi-permeable, hollow fiber tubes divide the hemofilter cartridge 208 into blood flow regions 205 within the hollow fiber tubes and a filtrate or permeate region 209 outside the hollow fiber tubes. As blood passes through blood regions 205, plasma water passes across the semi-permeable membranes of the hollow fiber tubes. The hemofilter cartridge 208 is a small hemofilter. More concentrated blood flows out from the cartridge 208 through molded flow path 210 and out of the manifold 200 through a blood outlet port 211. An air detector 212 is also integrated into blood return flow path 210.

The following are exemplary physical specifications of a hemofilter 208 in accordance with one embodiment of the present invention:

| | |
|---|---|
| Membrane Surface Area (m$^2$) | ≤0.1 |
| Prime Volume (ml) | ≤10 |
| Molecular Weight cut-off (Daltons) | 65,000 |
| Pressure Drop3 (mmHg) | ≤50 (Qb = 50 ml/min |
| Maximum Transmembrane Pressure (mmHg) | ≥500 |
| Overall Unit Length (cm) | 12-15 |
| Filtration rate | 8-10 ml/min @ 100 mmHg @ 50 ml/min Qb |
| Tubing Connections | |
| Blood | Male Luer |
| Filtrate | Slip fit (straight) |
| Sterilization: | ETO or gamma |
| Membrane Material: | Polysulfone (preferred) |
| Housing material | Polycarbonate |
| Potting material | Polyurethane |
| Sieving coefficients | |
| Urea | 1.00 |
| Creatinine | 1.00 |
| Vit B12 | 0.98 |
| Middle molecule/size | ≥0.20 17,000 |
| Albumin | ≤.03 |

Referring back to FIGS. 2a and 2b, ultrafiltrate waste from the permeate region 209 is drawn out by waste volumetric pump 213 through molded flow path 214, which, in one embodiment, has an integrated pressure sensor 215 located in-line of flow path 214. The ultrafiltrate waste is pumped through molded flow path 216, which, in one embodiment, has an integrated blood leak detector 217 and waste ultrafiltrate flow meter 218, in-line with flow path 216 leading out of the manifold 200 through a waste outlet port 219.

In one embodiment, the hemofilter cartridge 208 is disposable and can be removably integrated into the corresponding molded concavity in the manifold 200 to complete the ultrafiltration circuit. The manifold 200 also provides an interface to a redundant pinch valve to prevent air from entering the patient's vascular system. The pinch valve is designed such that it is in closed (occluded) position when no electrical power is applied.

The molded flow paths 202, 204, 210, 214 and 216 define the blood and ultrafiltrate flow circuits of the manifold 200. In one embodiment, these flow paths comprise disposable tubing and a plurality of interfacing components, such as joints, that are suitable for blood and ultrafiltrate contact for at least 3 days. The joints preferably are designed to have at least 5 lbs. strength and seal to 600 mmHg (that is, greater than hemofilter maximum trans-membrane pressure). In one embodiment, the blood set tubing corresponding to flow paths 202, 204 and 210 have suitable length and internal diameter for supplying a blood flow of 50 mL/minute. In one embodiment the prime volume of blood set tubing, including the hemofilter 205, is less than 40 mL. The blood set tubing interfaces with the blood volumetric pump 203. Blood pump 203 tubing, in one embodiment, is of Tygon brand, formulation S-50-HL, size ⅛" ID×³⁄₁₆" OD×¹⁄₃₂" Wall.

Similarly, in one embodiment, the ultrafiltrate set tubing corresponding to flow paths 214 and 216 are capable of supplying an ultrafiltrate flow of 500 mL/Hr (8.33 mL/minute). The ultrafiltrate set tubing also interfaces with the waste volumetric pump 213. Waste pump 213 tubing, in one embodiment, is of Tygon brand, formulation S-50-HL, size ³⁄₃₂" ID×⁵⁄₃₂" OD×¹⁄₃₂" Wall.

Since the ultrafiltration manifolds of the present invention comprise molded flow paths for blood, dialysate, waste fluids, and substitution fluids, the entire flow path can be easily manufactured as portable composite manifolds. The manifolds are also easy to handle since all flexible tubing outside the manifolds are attached on one side of the manifolds. Use of manifolds with built-in molded flow paths enhances failsafe treatment as the chances of disconnection, misassembly and leakage are minimized in comparison to prior art systems that use a myriad of flexible tubing. Use of the novel manifolds also enhances ease of use leading to enhanced portability.

In one embodiment the dialysis manifolds shown in FIGS. 1b and 2b are standalone compact units such that they can be individually and separately used to process blood from a patient. In another embodiment the two manifolds are connectable to each other to function as a dual stage blood processing system. In one example, blood is drawn from an arterial site in a patient and passed through a dialyzer where a large amount of waste fluid is convected out. The manifold is used to return an equal amount of fluid back to the blood, before the blood is reinfused. The manifold measures and dumps the waste fluid into a waste bag.

Figure 4:
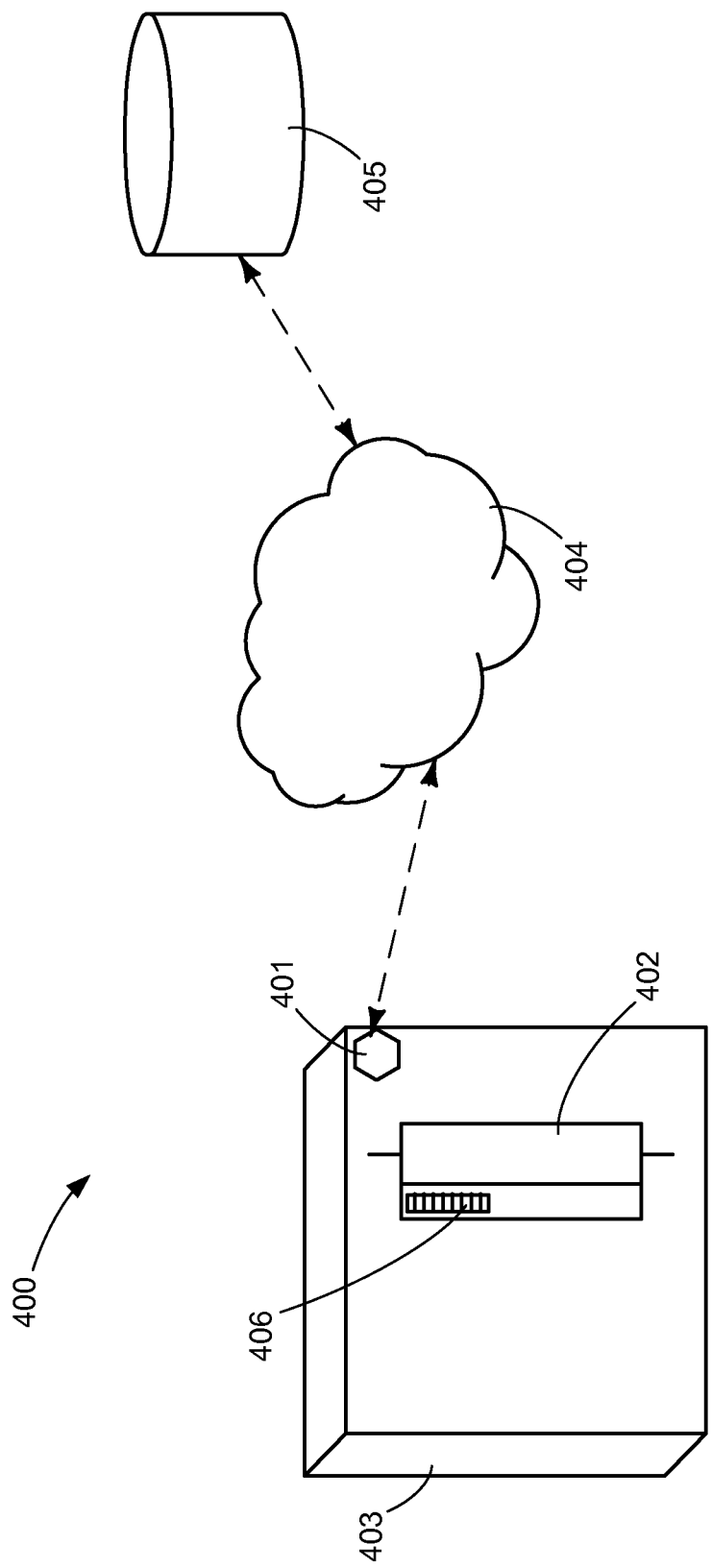
FIG. 4 is a functional block diagram showing one embodiment of an electronic-based lockout system of the present invention.

In another embodiment of the present invention, the novel manifolds described above also comprise an electronic-based lockout ("e-lockout") system. FIG. 4 is a functional block diagram showing one embodiment of the e-lockout system of the present invention. In one embodiment e-lockout system 400 comprises a reader 401 that detects and reads identification data 406 embedded in disposable items 402, such as disposable manifolds, disposable sorbents used in dialysate regeneration and/or dialyzers. The identification data 406 may be stored on disposable items 402 via barcode, RFID tags, EEPROM, microchip or any other identification means that uniquely identifies the disposable items 402 to be used in the dialysis system 403. The reader 401 is correspondingly a barcode reader, RFID reader, microchip reader, or any other reader that corresponds to the identification technology employed as is known to persons of ordinary skill in the art. In one embodiment, the reader 401 is connected with a transceiver for wirelessly connecting to a remote database 405 through a network 404 such as Internet or any other public or private network known to persons of ordinary skill in the art. In another embodiment, the reader 401 is directly aligned with the identification data 406 [not shown].

The database 405, located remote from the dialysis system, stores a plurality of information about the disposable items 402 that can be used in the system 403. The information comprises unique identification data 406 along with information for the corresponding disposable item such as authenticity, usability in terms of whether the item is likely to be in working condition, or not or if the item has been recalled by the manufacturer owing to a defect, its expiry date, if any, and/or any other such value-added information that would advantageously be evident to persons of ordinary skill in the art.

In operation, when a disposable item 402, such as a dialyzer, manifold, or a hemofilter cartridge, is loaded into the system 403 the reader 401 detects the disposable item 402 through identification data 406 embedded onto item 402. This identification data 406 is read by reader 401, which, in turn, communicates, either wired or wirelessly, with database 405 to request more information on the item 402 stored therein, based on identification data 406, or confirm the validity or integrity of the item 402 based on identification data 406.

For example, in one embodiment, dialyzer cartridge 402 identified by the reader 401 may have been called back by the manufacturer on account of some defect. This call-back information is stored on the database 405 and is returned back to the reader 401 as a result of the request signal sent by the reader 401 to the database 405 trough the network 404. As a result of the call-back information received from the database 405 the microprocessor controlling the blood purification system supported by the system 403 does not allow the user to proceed with treatment. This is achieved, in one embodiment, by suspending functioning of the pumps that propel fluids through the fluid circuits of the blood purification system 403. Additionally, an audio/visual alarm may also be displayed to this effect.

In another example, dialyzer cartridge 402 identified by the reader 401 may not be authentic as a result of which; the microprocessor would not allow functioning of the blood purification system of the system 403. Thus, the e-lockout system 400 of the present invention prevents usage of the system 403 in case the disposable items 402 attached to the manifold 403 are in a compromised state.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

The invention claimed is:

1. A disposable apparatus for use in filtering blood comprising:
   a molded plastic substrate having a first flow path and a second flow path formed therein, wherein said first flow path and second flow path are fluidically isolated from each other, wherein the molded plastic substrate comprises a plurality of concave spaces;
   a hemofilter cartridge positioned within a first of said plurality of concave spaces and in fluid communication with said first flow path and said second flow path;
   at least one sensor positioned within a second of said plurality of concave spaces;
   a plurality of ports integrated into said molded plastic substrate;
   a plurality of interfacing components, each of said interfacing components configured to have at least 5 pounds of strength and a seal up to 600 mmHg; and
   embedded data, wherein said embedded data uniquely identifies the disposable apparatus and wherein said disposable apparatus is caused to be unusable based on said embedded data.

2. The disposable apparatus of claim 1 further comprising tubing having a first end fixedly attached to at least one of said ports and a second end adapted to be removably attached to an input port of a collection reservoir.

3. The disposable apparatus of claim 2 further comprising tubing having a first end fixedly attached to at least one of said ports and a second end adapted to be removably attached to an input port of a dialysate regeneration system.

4. A disposable apparatus for use in filtering blood comprising:
   a plastic substrate comprising a plurality of molded concave spaces;
   first and second inlet ports positioned in the plastic substrate;
   first and second outlet ports positioned in the plastic substrate;
   a first flow path formed in the plastic substrate wherein said first flow path forms a pathway for transporting blood from the first inlet port to the first outlet port;
   a first sensor positioned directly in the first flow path;
   a second flow path formed in the plastic substrate wherein said second flow path forms a pathway for transporting a first fluid from the second inlet port to the second outlet port;
   a second sensor positioned directly in the second flow path;
   a hemofilter cartridge positioned within a first of said plurality of concave spaces and in fluid communication with said first flow path and said second flow path;
   a plurality of interfacing components, each of said interfacing components configured to have at least 5 pounds of strength and a seal up to 600 mmHg; and
   embedded data, wherein said embedded data uniquely identifies the disposable apparatus and wherein said disposable apparatus is caused to be unusable based on said embedded data.

5. The disposable apparatus of claim 4 further comprising tubing having a first end fixedly attached to the second outlet port and a second end adapted to be removably attached to an input port of a collection reservoir.

6. The disposable apparatus of claim 4 further comprising:
   a third inlet port;
   a third outlet port; and
   a third flow path formed in the plastic substrate comprising at least one sensor directly molded therein wherein said third flow path forms a pathway for transporting blood from the third inlet port to the third outlet port.

7. The disposable apparatus of claim 6 further comprising tubing having a first end fixedly attached to the third outlet port and a second end adapted to be removably attached to an input port of a dialysate regeneration system.

8. The disposable apparatus of claim 4 wherein said sensor comprises a transducer diaphragm.

9. The disposable apparatus of claim 8 wherein said transducer diaphragm comprises polyisoprene.

10. A disposable apparatus for use in filtering blood comprising:
    a molded plastic substrate having a first flow path and a second flow path formed therein, wherein said first flow path and second flow path are fluidically isolated from each other, wherein the molded plastic substrate comprises a plurality of concave spaces;
    at least one sensor molded into at least one of the first or second flow paths using a multi-shot plastic injection molding process;
    a plurality of ports integrated into said molded plastic substrate;
    a hemofilter cartridge positioned within a first of said plurality of concave spaces and in fluid communication with said first flow path and said second flow path;

a plurality of interfacing components, each of said interfacing components configured to have at least 5 pounds of strength and a seal up to 600 mmHg; and embedded data, wherein said embedded data uniquely identifies the disposable apparatus and wherein said disposable apparatus is caused to be unusable based on said embedded data.

11. The disposable apparatus of claim 10 wherein said sensor comprises a transducer diaphragm.

12. The disposable apparatus of claim 10 further comprising tubing having a first end fixedly attached to at least one of said ports and a second end adapted to be removably attached to an input port of a collection reservoir.

13. The disposable apparatus of claim 10 further comprising tubing having a first end fixedly attached to at least one of said ports and a second end adapted to be removably attached to an input port of a dialysate regeneration system.

\* \* \* \* \*